(12) United States Patent
Banerjee et al.

(10) Patent No.: US 9,798,856 B2
(45) Date of Patent: Oct. 24, 2017

(54) CLINICAL WORKSTATION INTEGRATING MEDICAL IMAGING AND BIOPSY DATA AND METHODS USING SAME

(71) Applicant: KONINKLIJKE PHILIPS N.V., Eindhoven (NL)

(72) Inventors: Nilanjana Banerjee, Armonk, NY (US); Sitharthan Kamalakaran, Pelham, NY (US); Vinay Varadan, New York, NY (US); Angel Janevski, New York, NY (US); Nevenka Dimitrova, Pelham Manor, NY (US)

(73) Assignee: Koninklijke Philips N.V., Eindhoven (NL)

( * ) Notice: Subject to any disclaimer, the term of this patent is extended or adjusted under 35 U.S.C. 154(b) by 236 days.

(21) Appl. No.: 14/383,761

(22) PCT Filed: Mar. 20, 2013

(86) PCT No.: PCT/IB2013/052224
§ 371 (c)(1),
(2) Date: Sep. 8, 2014

(87) PCT Pub. No.: WO2013/140357
PCT Pub. Date: Sep. 26, 2013

(65) Prior Publication Data
US 2015/0097868 A1      Apr. 9, 2015

Related U.S. Application Data

(60) Provisional application No. 61/613,640, filed on Mar. 21, 2012.

(51) Int. Cl.
*G09G 5/00* (2006.01)
*G06F 19/00* (2011.01)

(52) U.S. Cl.
CPC .......... *G06F 19/321* (2013.01); *G06F 19/366* (2013.01)

(58) Field of Classification Search
CPC ...................................................... G06F 19/321
See application file for complete search history.

(56) References Cited

U.S. PATENT DOCUMENTS 5,066,278 A * 11/1991 Hirschberg ....... A61M 5/14276
604/246
5,227,969 A * 7/1993 Waggener .............. A61N 5/103
600/407

(Continued)

FOREIGN PATENT DOCUMENTS

WO         2009153723 A1     12/2009

OTHER PUBLICATIONS

O'Connor, JPB et al. "DCE-MRI biomarkers of tumour heterogeneity predict CRC liver metastasis shrinkage following bevacizumab and FOLFOX-6", British Journal of Cancer, vol. 105, pp. 139-145 (2011).

(Continued)

*Primary Examiner* — Devona E Faulk
*Assistant Examiner* — Charles L Beard

(57) ABSTRACT

An imaging visualization workstation (30) includes a graphical display device (32) and an electronic data processor, and is configured to perform a method including: spatially registering a biopsy sample extracted from a medical subject with a medical image (12) of the medical subject; combining the medical image with a graphical representation of information (20, 22) generated from the biopsy sample to generate a combined image in which the graphical representation is spatially delineated based on the spatial registration of the biopsy sample; and displaying the combined image on the graphical display device of the imaging visualization workstation. A method comprises extracting a (Continued)

biopsy sample spatial sample from a medical subject, processing the biopsy sample to generate biopsy information, acquiring a medical image of the subject, spatially registering the biopsy sample with the medical image, and displaying the medical image modified to include an annotation generated from the biopsy information.

18 Claims, 10 Drawing Sheets

(56) References Cited

U.S. PATENT DOCUMENTS

| | | | | |
|---|---|---|---|---|
| 6,151,404 | A * | 11/2000 | Pieper | G06F 19/321 382/128 |
| 6,254,538 | B1 * | 7/2001 | Downey | A61B 8/0825 128/915 |
| 6,611,630 | B1 * | 8/2003 | Miller | G06K 9/48 382/128 |
| 6,676,658 | B2 * | 1/2004 | Burbank | A61B 10/0266 606/41 |
| 6,722,371 | B1 * | 4/2004 | Fogarty | A61B 90/39 128/899 |
| 6,846,282 | B1 * | 1/2005 | Ford | A61N 5/1007 600/1 |
| 6,847,700 | B1 * | 1/2005 | Mitra | A61N 5/1001 378/145 |
| 7,588,528 | B2 * | 9/2009 | Drobnik | A61N 5/1027 600/3 |
| 7,606,405 | B2 * | 10/2009 | Sawyer | A61N 5/1049 378/65 |
| 7,630,750 | B2 * | 12/2009 | Liang | G06F 19/3437 128/922 |
| 7,776,310 | B2 * | 8/2010 | Kaplan | A61B 90/39 424/1.25 |
| 8,260,013 | B2 * | 9/2012 | Pekar | A61B 6/032 250/363.04 |
| 8,270,698 | B2 * | 9/2012 | Geiger | G06T 7/68 382/100 |
| 8,306,185 | B2 * | 11/2012 | Bal | A61N 5/103 378/65 |
| 8,363,784 | B2 * | 1/2013 | Sobering | A61N 5/1031 378/64 |
| 8,520,932 | B2 * | 8/2013 | Cool | G06T 17/10 382/128 |
| 8,768,021 | B2 * | 7/2014 | Yu | G06T 7/0012 382/128 |
| 9,101,395 | B2 * | 8/2015 | Gutierrez | A61B 19/5244 |
| 9,271,794 | B2 * | 3/2016 | Tyc | A61B 18/22 |
| 9,277,955 | B2 * | 3/2016 | Herscher | A61B 18/1492 |
| 9,339,243 | B2 * | 5/2016 | Zhang | A61B 6/025 |
| 9,384,566 | B2 * | 7/2016 | Chen | G06T 11/006 |
| 9,393,445 | B2 * | 7/2016 | Yamada | A61N 5/1039 |
| 9,555,263 | B2 * | 1/2017 | Groke | A61N 5/1071 |
| 9,669,117 | B2 * | 6/2017 | Campbell | A61K 49/0442 |
| 2002/0039401 | A1 * | 4/2002 | Salb | A61B 6/4035 378/98.9 |
| 2002/0059938 | A1 * | 5/2002 | Fogarty | A61B 90/39 128/899 |
| 2002/0099264 | A1 * | 7/2002 | Fontenot | A61B 90/11 600/130 |
| 2003/0092957 | A1 * | 5/2003 | Scott | A61N 5/1007 600/3 |
| 2003/0135115 | A1 * | 7/2003 | Burdette | A61B 8/12 600/437 |
| 2005/0041843 | A1 * | 2/2005 | Sawyer | A61N 5/1049 382/128 |
| 2005/0078857 | A1 * | 4/2005 | Park | A61B 5/0002 382/128 |
| 2005/0080333 | A1 * | 4/2005 | Piron | A61B 8/0825 600/417 |
| 2006/0009686 | A1 * | 1/2006 | Boukas | A61B 5/444 600/315 |
| 2006/0025669 | A1 * | 2/2006 | Ramamurthy | G06T 5/50 600/407 |
| 2006/0030768 | A1 * | 2/2006 | Ramamurthy | G06T 7/0012 600/407 |
| 2006/0206105 | A1 * | 9/2006 | Chopra | A61B 5/055 606/27 |
| 2006/0258933 | A1 * | 11/2006 | Ellis | A61N 5/103 600/407 |
| 2007/0005249 | A1 * | 1/2007 | Dupree | G01S 13/89 702/3 |
| 2007/0100226 | A1 * | 5/2007 | Yankelevitz | A61B 5/1075 600/407 |
| 2007/0239062 | A1 * | 10/2007 | Chopra | A61B 5/01 600/549 |
| 2007/0280418 | A1 * | 12/2007 | Weil | A61K 51/04 378/65 |
| 2008/0004526 | A1 * | 1/2008 | Gross | A61B 8/0825 600/437 |
| 2008/0143718 | A1 * | 6/2008 | Ray | G06K 9/4638 345/424 |
| 2008/0186378 | A1 * | 8/2008 | Shen | A61B 8/0833 348/65 |
| 2008/0194985 | A1 * | 8/2008 | Nicoson | A61B 17/3468 600/566 |
| 2008/0221929 | A1 | 9/2008 | Brackett | |
| 2008/0292164 | A1 * | 11/2008 | Azar | A61B 5/0091 382/131 |
| 2008/0303818 | A1 * | 12/2008 | Moriya | G06T 7/174 345/427 |
| 2009/0011032 | A1 * | 1/2009 | LePivert | A61B 18/02 424/490 |
| 2009/0087047 | A1 * | 4/2009 | Moriya | A61B 5/7425 382/128 |
| 2009/0112086 | A1 * | 4/2009 | Melman | A61B 6/037 600/431 |
| 2009/0116718 | A1 * | 5/2009 | Goto | A61B 5/055 382/131 |
| 2009/0118640 | A1 * | 5/2009 | Miller | A61B 90/36 600/567 |
| 2009/0196480 | A1 * | 8/2009 | Nields | G06T 7/33 382/132 |
| 2009/0253978 | A1 * | 10/2009 | Hashimshony | A61B 5/064 600/407 |
| 2009/0306504 | A1 * | 12/2009 | Arai | A61B 6/466 600/443 |
| 2010/0030211 | A1 * | 2/2010 | Davalos | A61N 1/327 606/41 |
| 2010/0056844 | A1 * | 3/2010 | Fisher | A61K 9/0024 600/8 |
| 2010/0087756 | A1 * | 4/2010 | Egorov | A61B 5/0053 600/587 |
| 2010/0106056 | A1 * | 4/2010 | Norris | A61B 8/0841 600/567 |
| 2010/0128946 | A1 * | 5/2010 | Fidrich | G06T 7/0087 382/131 |
| 2010/0159497 | A1 * | 6/2010 | Kimia | G06T 7/0012 435/29 |
| 2010/0172559 | A1 * | 7/2010 | Kumar | A61B 10/0241 382/131 |
| 2010/0250275 | A1 * | 9/2010 | Sakagawa | G06F 19/321 705/2 |
| 2010/0266179 | A1 * | 10/2010 | Ramsay | G06T 7/0012 382/131 |
| 2010/0292558 | A1 * | 11/2010 | Saadat | A61B 1/00085 600/407 |
| 2010/0298705 | A1 * | 11/2010 | Pelissier | A61B 5/06 600/443 |
| 2010/0322490 | A1 * | 12/2010 | Pan | A61B 5/0088 382/128 |
| 2011/0009748 | A1 * | 1/2011 | Greene | A61B 8/08 600/439 |
| 2011/0021888 | A1 * | 1/2011 | Sing | A61B 5/0507 600/302 |
| 2011/0026768 | A1 * | 2/2011 | Chari | G06T 7/0016 382/103 |

(56) References Cited

U.S. PATENT DOCUMENTS

| | | | |
|---|---|---|---|
| 2011/0064658 A1* | 3/2011 | Scherz | A61K 49/0036 424/1.69 |
| 2011/0075901 A1* | 3/2011 | Nakamura | G06F 19/321 382/128 |
| 2011/0075913 A1* | 3/2011 | Moriya | G06F 19/321 382/132 |
| 2011/0085713 A1* | 4/2011 | Yan | G06T 7/0081 382/128 |
| 2011/0103657 A1* | 5/2011 | Kang | G06T 7/74 382/128 |
| 2011/0158491 A1* | 6/2011 | Markova | G06T 3/0081 382/128 |
| 2011/0191082 A1* | 8/2011 | Blezek | A61B 18/02 703/11 |
| 2011/0208052 A1* | 8/2011 | Entrekin | A61B 8/0825 600/437 |
| 2011/0268339 A1* | 11/2011 | Volokh | A61B 6/502 382/132 |
| 2011/0313288 A1* | 12/2011 | Chi Sing | A61B 5/0507 600/437 |
| 2012/0014578 A1* | 1/2012 | Karssemeijer | G06T 7/0012 382/131 |
| 2012/0065494 A1* | 3/2012 | Gertner | A61B 5/055 600/411 |
| 2012/0105480 A1* | 5/2012 | Barley | A61B 90/36 345/641 |
| 2012/0123189 A1* | 5/2012 | Ribbing | A61K 51/1255 600/8 |
| 2012/0143167 A1* | 6/2012 | Morrison | A61B 18/02 604/500 |
| 2012/0157841 A1* | 6/2012 | Glaenzer | A61B 8/12 600/439 |
| 2012/0176408 A1* | 7/2012 | Moriya | A61B 5/0013 345/629 |
| 2012/0183188 A1* | 7/2012 | Moriya | G06F 19/321 382/128 |
| 2012/0262453 A1* | 10/2012 | Endo | A61B 8/483 345/419 |
| 2013/0030408 A1* | 1/2013 | Piferi | A61B 5/055 604/500 |
| 2013/0072784 A1* | 3/2013 | Velusamy | A61B 18/12 600/424 |
| 2013/0090554 A1* | 4/2013 | Zvuloni | A61B 10/0241 600/424 |
| 2013/0109024 A1* | 5/2013 | Rajagopalan | G01N 1/2813 435/6.12 |
| 2013/0114867 A1* | 5/2013 | Kondo | G06F 19/321 382/128 |
| 2013/0116548 A1* | 5/2013 | Kumar | A61B 8/0841 600/424 |
| 2013/0131517 A1* | 5/2013 | Panasyuk | A61B 5/0059 600/473 |
| 2013/0217950 A1* | 8/2013 | Partanen | G01R 33/4814 600/1 |
| 2013/0251633 A1* | 9/2013 | Borden | A61B 8/085 424/9.2 |
| 2013/0289393 A1* | 10/2013 | Kruecker | A61B 8/0841 600/424 |
| 2014/0037177 A1* | 2/2014 | Endo | G06T 7/0028 382/131 |
| 2014/0094698 A1* | 4/2014 | Burbank | A61K 49/006 600/431 |
| 2014/0140593 A1* | 5/2014 | Park | G06F 19/345 382/128 |
| 2014/0242118 A1* | 8/2014 | Strober | A61K 39/0011 424/277.1 |
| 2014/0257262 A1* | 9/2014 | Carpentier | A61N 7/02 606/28 |
| 2014/0303423 A1* | 10/2014 | Amthor | A61N 5/1027 600/8 |
| 2014/0309522 A1* | 10/2014 | Fullerton | A61B 5/064 600/424 |
| 2014/0330162 A1* | 11/2014 | Chakrabarti | A61B 10/02 600/562 |
| 2015/0031990 A1* | 1/2015 | Boctor | A61B 34/20 600/424 |
| 2015/0141905 A1* | 5/2015 | Spears | A61M 5/1407 604/24 |
| 2015/0148677 A1* | 5/2015 | Mullick | A61B 8/5223 600/443 |
| 2015/0196274 A1* | 7/2015 | Yamamoto | A61B 8/485 600/442 |
| 2015/0223901 A1* | 8/2015 | Wei | G06F 19/321 703/11 |
| 2015/0245825 A1* | 9/2015 | Stone | A61B 90/39 600/567 |
| 2015/0282782 A1* | 10/2015 | Zhao | A61B 8/0825 600/443 |
| 2015/0327941 A1* | 11/2015 | Haynes | A61B 90/02 600/3 |
| 2015/0356730 A1* | 12/2015 | Grove | G01N 23/046 382/124 |
| 2015/0375012 A1* | 12/2015 | Herskovic | A61N 5/1015 600/431 |
| 2016/0000520 A1* | 1/2016 | Lachmanovich | A61B 34/20 600/424 |
| 2016/0055636 A1* | 2/2016 | Khalil | A61B 5/726 424/85.2 |
| 2016/0063699 A1* | 3/2016 | Gustafson | G06F 19/321 715/738 |
| 2016/0074626 A1* | 3/2016 | Weadock | A61M 25/0169 600/3 |
| 2016/0078614 A1* | 3/2016 | Ryu | G06T 7/0012 382/128 |
| 2016/0213949 A1* | 7/2016 | Uhlemann | A61N 5/1001 |
| 2016/0232668 A1* | 8/2016 | Ishiraha | A61B 6/032 |
| 2016/0235296 A1* | 8/2016 | Dunning | A61B 3/12 |
| 2016/0253468 A1* | 9/2016 | Osawa | G06F 19/321 |
| 2016/0300017 A1* | 10/2016 | Lee | G06F 19/321 |
| 2016/0314589 A1* | 10/2016 | Nagao | G06F 19/321 |
| 2016/0321427 A1* | 11/2016 | Bogoni | G06F 19/3443 |
| 2017/0119334 A1* | 5/2017 | Smith | A61B 6/5211 |

OTHER PUBLICATIONS

Navin, N. et al., "Tumour evolution inferred by single-cell sequencing", Nature vol. 472, pp. 90-95 (2011).

Penn, A. et al. "Morphologic Blooming in Breast MRI as a characterization of Margin for Discriminating Benign from Malignant Lesions," Acad Radiol 2006; 13:1344-1354.

Fischer, DR et al., "Is the 'blooming sign' a promising additional tool to determine malignancy in MR mammography?", Eur Radiol (2004) 14:394-401.

\* cited by examiner

CLINICAL WORKSTATION INTEGRATING MEDICAL IMAGING AND BIOPSY DATA AND METHODS USING SAME

CROSS-REFERENCE TO PRIOR APPLICATIONS

This application is the U.S. National Phase application under 35 U.S.C. §371 of International Application No. PCT/IB2013/052224, filed on Mar. 20, 2013, which claims the benefit of U.S. Provisional Application No. 61/613,640 filed on Mar. 21, 2012 and European Application No. 12160984.6 filed on Mar. 21, 2012. These applications are hereby incorporated by reference herein.

The following relates to the medical arts, oncology arts, medical imaging arts, biopsy and pathology arts, and related arts.

Medical imaging is used in oncology and other medical areas to provide noninvasive or minimally invasive characterization of structural and/or functional aspects of a cancerous tumor, an organ containing metastasized cancerous cells, or other anatomical structures of interest. Various medical imaging modalities are known and exploited for their diverse imaging capabilities. Some imaging modalities used in various types of medical imaging include: magnetic resonance (MR) imaging; positron emission tomography (PET) imaging; single photon emission computed tomography (SPECT); transmission computed tomography (CT) or other transmission x-ray imaging techniques; and so forth. Some examples of imaging techniques include: static anatomical imaging (with or without an exogenous contrast agent); bolus imaging (where a vascular contrast agent bolus is administered and intake, washout, or other dynamics of the contrast agent is observed); functional MR imaging (fMRI, e.g. observing oxygenation state of brain tissue during functional activities); targeted contrast agent imaging (e.g., PET or SPECT imaging of a radioisotope that preferentially collects in a tissue type of interest); and so forth. Medical imaging also has some limited capabilities in terms of detecting macroscopic imaging biomarkers that are indicative of certain oncological conditions. For example, MRI biomarkers of tumor heterogeneity have been shown to be predictive of response to therapy. See O'Connor et al., "DCE-MRI biomarkers of tumour heterogeneity predict CRC liver metastasis shrinkage following bevacizumab and FOLFOX-6", British Journal of Cancer vol. 105 pages 139-145 (2011). However, it has been recognized that such imaging analyses can over-simplify the tumour biology, and could be advantageously augmented by other techniques such as microvascular heterogeneity measurements. See Id.

Invasive techniques employ a biopsy procedure to extract tissue that conventionally undergoes histopathology analysis (e.g., tissue sectioning, staining, and microscopic analysis). Histopathology enables unambiguous identification of tissue type, and in particular enables identification of whether a tumor is malignant (i.e., cancer) or benign. The biopsy sample can be acquired by completely removing the tumor or other anatomical feature of interest (incisional biopsy), but this approach is highly invasive and is generally not recommended unless there is a reasonable probability that the entire suspect mass can be removed. Alternatively, incisional or core biopsy techniques can be employed in which an interventional instrument removes only a portion of the tumor, e.g. a core sample acquired using a hollow needle or other interventional instrument. These approaches preserve the structural integrity of the sample. In needle aspiration biopsy the sample is drawn in a manner that does not preserve its structural integrity (e.g., well suited for acquiring a fluid sample that has no particular structure).

Molecular analyses have also been developed, which provide further tools for the oncologist. In these techniques, a biopsy sample is processed to assess genetic and/or proteomic information. Molecular tests have been developed for specific molecular markers, and for sets of molecular markers, the latter sometimes being performed in massively parallel fashion using a microarray or similar apparatus to concurrently assess dozens, hundreds, or more molecular markers using a single tissue sample. The molecular marker or set of markers is typically analyzed using a threshold or algorithm that outputs a clinically useful result respective to a specific medical condition. For example, a particular molecular marker or set of markers may be indicative of a particular type of cancer, or may measure the activity of a molecular signaling pathway associated with a known physical process, or so forth. Genetic sequencing techniques have also been developed that measure DNA and/or RNA sequences, sometimes up to and including the entire genome of the tissue (i.e., whole genome sequencing or WGS). Genetic sequencing techniques provide vast quantities of data for molecular analyses, which can be used in conventional molecular tests and/or in "discovery" analysis modalities in which the genetic data is searched in an effort to discover probative genetic features.

In a typical (simplified) oncological workflow, a screening test or physical examination reveals a suspected cancerous condition. Medical imaging is then performed to identify tumors or lesions in the suspect organ or tissue, or to provide anatomical characterization of a previously identified tumor (e.g., in the case of a suspicious breast lump identified by physical examination). The medical imaging is followed by a biopsy procedure that removes a sample of the imaged tumor, and histopathology and/or molecular tests are performed on the biopsy sample to determine whether the tumor is malignant and, if so, to assess the type of cancer. Treatment in the form of chemotherapy, brachytherapy, radiation therapy, or so forth is then applied based on the imaging and biopsy results. For example, if the biopsy indicates estrogen receptor (ER) positive breast cancer, then treatment that suppresses estrogen levels in the patient may be employed. These treatments are interlaced with further medical imaging sessions to assess whether the treatments are effective in reducing the tumor size. Further biopsies may also be performed to check for metastasis not detectable by the imaging.

In this workflow, the medical imaging and biopsy procedures provide complementary information, with the imaging providing spatial or anatomical information and the biopsy providing tissue identification and characterization. The imaging may also be used to provide some indirect tissue information for example, bolus imaging can assess vascular density which can be suggestive of angiogenesis associated with cancer growth. Although indirect, such imaging information has the advantage of being minimally invasive (involving injection of a vascular contrast agent bolus) and providing spatially delineated information.

However, existing medical approaches do not effectively integrate the medical imaging and biopsy workflows. Conventionally, the information generated by medical imaging and biopsy, respectively, is generated separately and is combined manually by the physician who takes into account the collected imaging, histopathology, and/or molecular analysis information in assessing the patient case. At most, the imaging may be used to identify a biopsy site, and the skilled physician may manually guide some degree of workflow integration by ordering interleaved imaging and biopsy procedures over the course of the patient treatment in a manner that generates complementary information.

The following contemplates improved apparatuses and methods that overcome the aforementioned limitations and others.

According to one aspect, an imaging visualization workstation includes a graphical display device and an electronic data processor. The imaging visualization workstation is configured to perform a method including: spatially registering a biopsy sample extracted from a medical subject with a medical image of the medical subject; combining the medical image with a graphical representation of information generated from the biopsy sample to generate a combined image in which the graphical representation is spatially delineated based on the spatial registration of the biopsy sample; and displaying the combined image on the graphical display device of the imaging visualization workstation.

According to another aspect, a method comprises: performing a biopsy procedure to extract a biopsy sample from a medical subject; processing the biopsy sample to generate biopsy information; acquiring a medical image of the subject; spatially registering the biopsy sample with the medical image; and displaying on a graphical display device the medical image modified to include an annotation generated from the biopsy information.

According to another aspect, a non-transitory storage medium stores instructions executable by an electronic data processing device to perform operations including (i) identifying a region of a medical image of a medical subject that depicts a location of the medical subject from which a biopsy sample was extracted and (ii) modifying the medical image to include at least one annotation of the identified region wherein the annotation is based on biopsy information generated from the biopsy sample.

One advantage resides in providing synergistic integration of imaging and biopsy information.

Another advantage resides in providing spatial mapping of biopsy information based on imaging data.

Numerous additional advantages and benefits will become apparent to those of ordinary skill in the art upon reading the following detailed description.

The invention may take form in various components and arrangements of components, and in various process operations and arrangements of process operations. The drawings are only for the purpose of illustrating preferred embodiments and are not to be construed as limiting the invention.

FIG. 1 diagrammatically shows an oncology workflow including an imaging visualization workstation that integrates medical images and information obtained by processing biopsy samples.

FIG. 2 diagrammatically shows illustrative extraction of biopsy samples from two lesions of a breast that are known or suspected to be malignant.

FIGS. 3-5 diagrammatically show three alternative graphical display configurations that each combine a medical image of the two breast lesions of FIG. 2 with a graphical representation of antigen Ki-67 level values obtained from analysis of biopsy samples extracted from the two lesions.

FIG. 6 diagrammatically shows a biopsy core obtained using an interventional instrument having a hollow needle for extracting the biopsy core.

FIG. 7 diagrammatically shows the lesion from which the biopsy core of FIG. 6 is extracted, with a dashed line indicating the biopsy needle trajectory. Also indicated is the length ($L_{core}$) of the biopsy core.

FIG. 8 diagrammatically shows spatial registration of the biopsy core of FIG. 6 in the lesion of FIG. 7, where the spatial registration utilizes the lesion boundary identifiable in the biopsy core as a reference feature.

Figure 6:
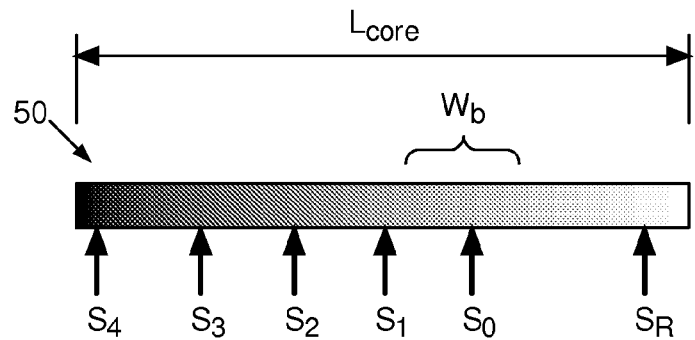
Figure 7:
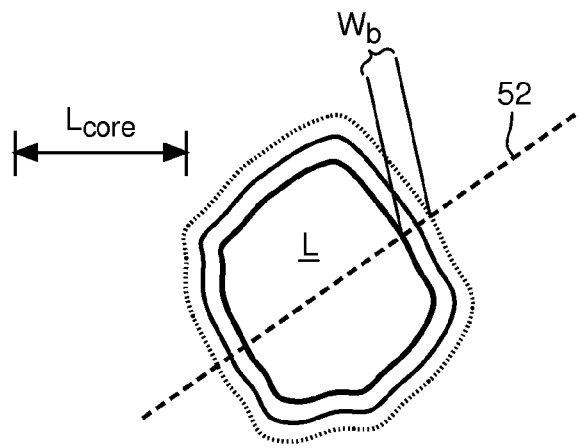
Figure 11:
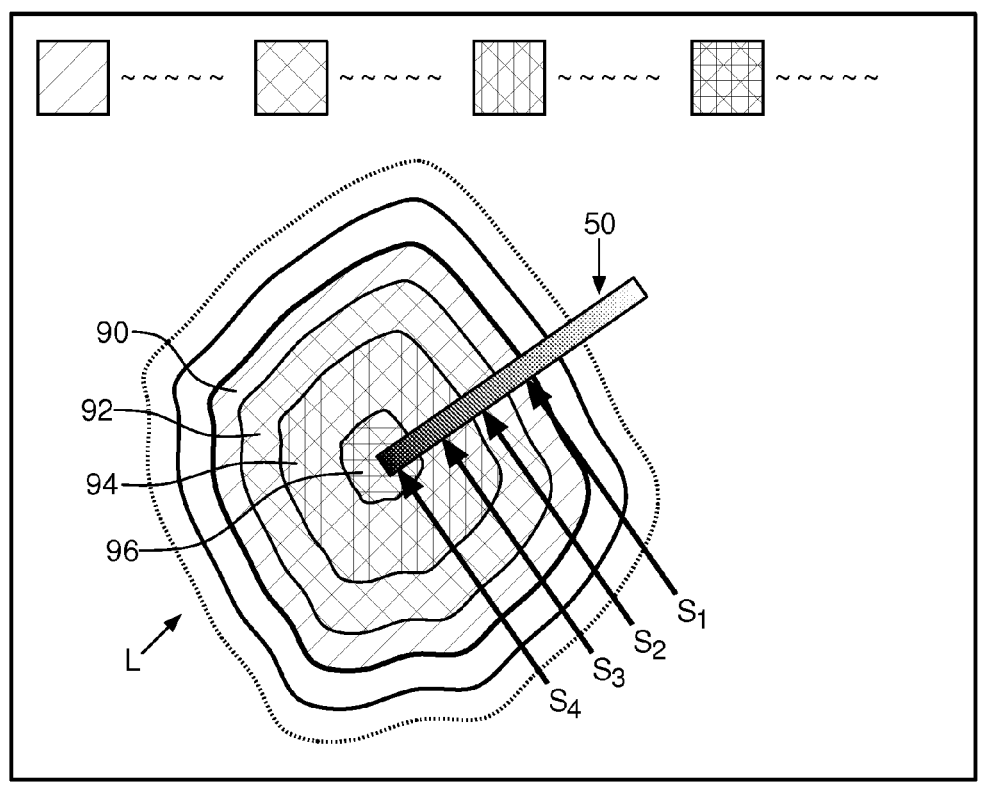

FIG. 11 diagrammatically shows allocation of contiguous regions of the lesion of FIG. 7 to the biopsy samples sectioned from the biopsy core of FIG. 6. The allocation employs an assumption of approximate spherical symmetry of the lesion.

Figure 12:
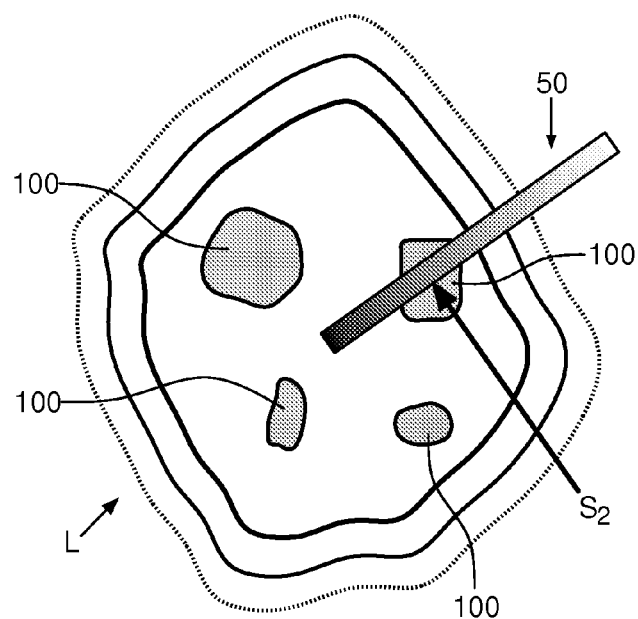

FIG. 12 diagrammatically shows an allocation of a lesion region comprising multiple discontinuous portions of the lesion to the biopsy sample $S_2$ sectioned from the biopsy core of FIG. 6.

Figure 13:
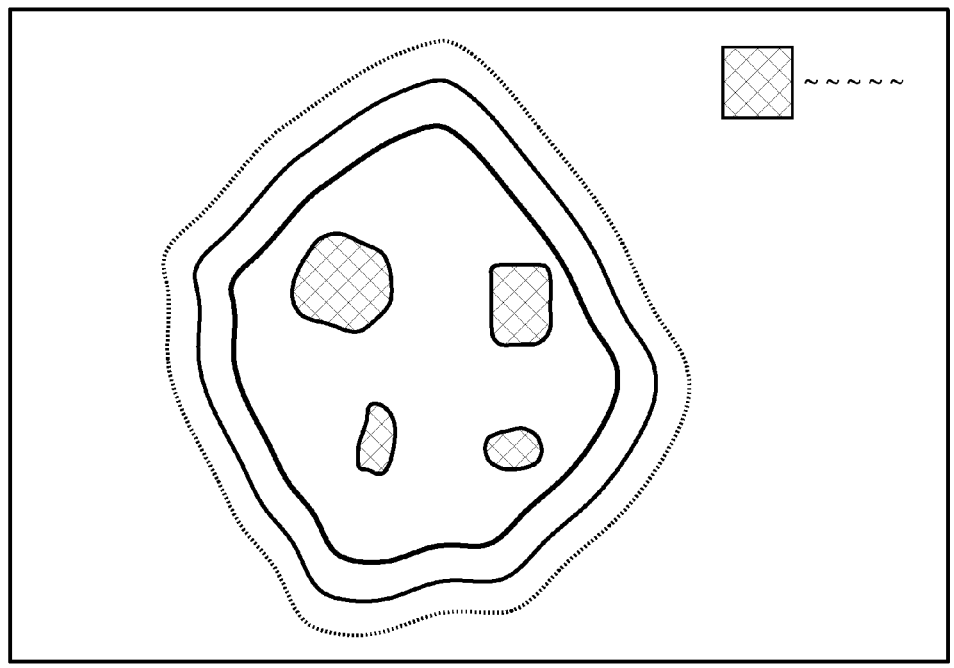

FIG. 13 diagrammatically shows a combined image comprising the medical image with the lesion region of multiple discontinuous portions of FIG. 12 false colored or highlighted based on information obtained from biopsy sample $S_2$.

Figure 14:
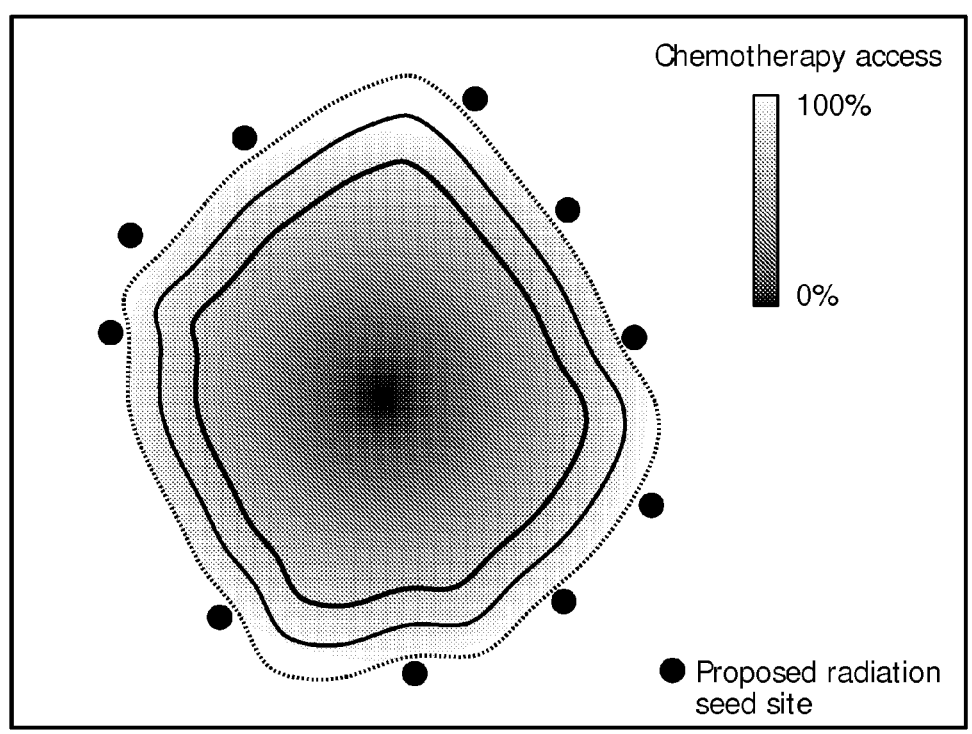

FIG. 14 diagrammatically shows a combined image comprising the medical image overlaid with a chemotherapy access map computed based on microvasculature information obtained from biopsy samples and the size and shape of the lesion as depicted in the medical image.

Figure 15:
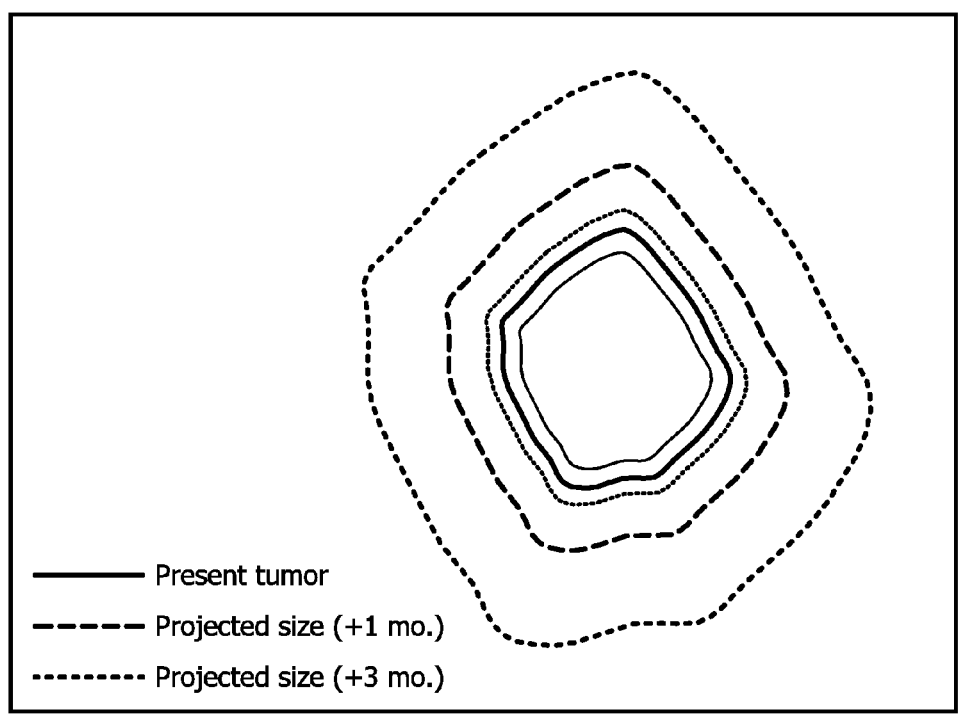

FIG. 15 diagrammatically shows a combined image comprising the medical image rendered at low intensity or "grayed out" and overlaid with projected tumor sizes computed based on combination of lesion tissue growth rate estimated from biopsy samples and the present size and shape of the lesion as shown by the medical image.

Figure 1:
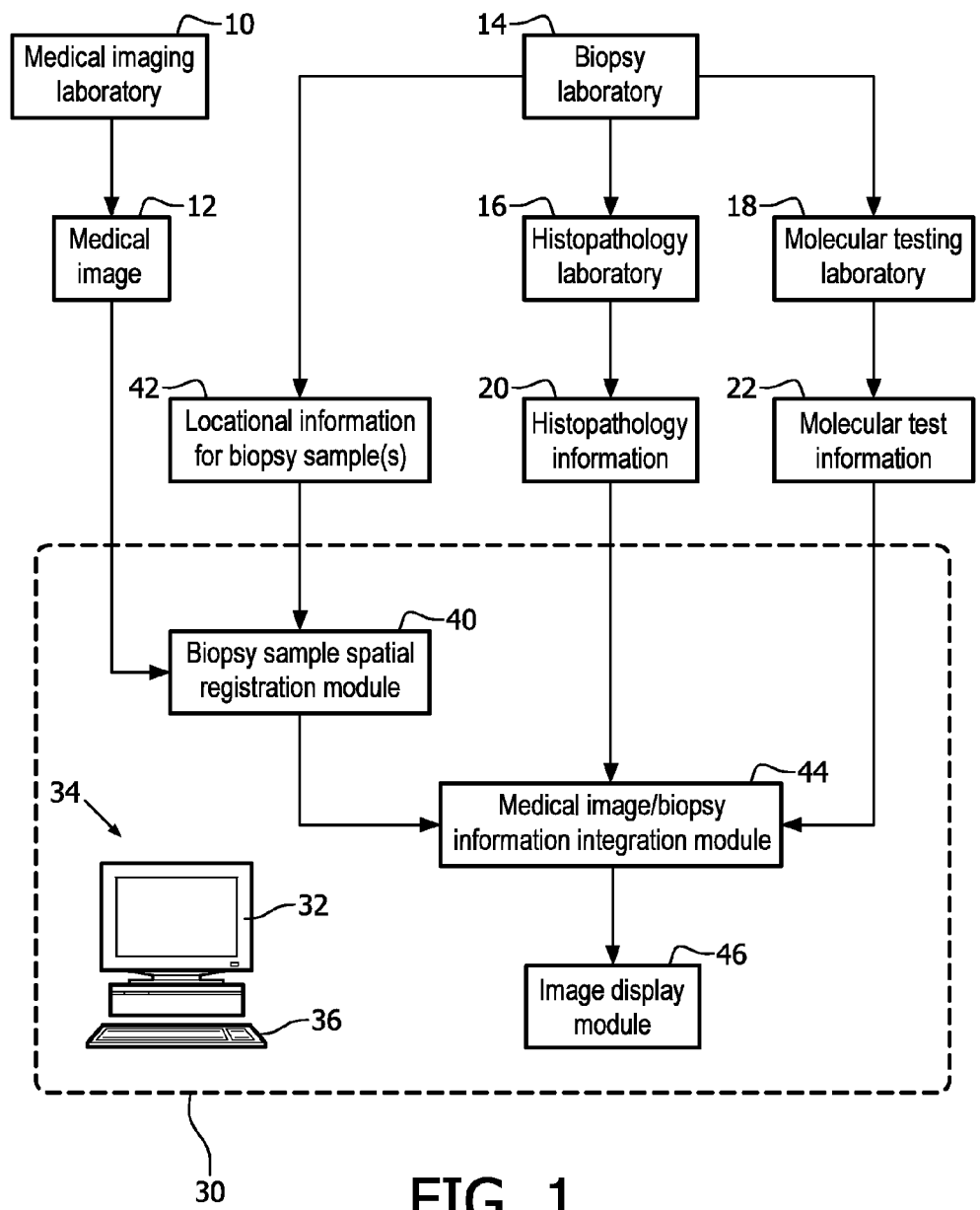

With reference to FIG. 1, a medical imaging laboratory 10 acquires a medical image 12 of a medical subject using a suitable imaging modality such as magnetic resonance (MR) imaging, positron emission tomography (PET) imaging, single photon emission computed tomography (SPECT), transmission computed tomography (CT) or other transmission x-ray imaging techniques, or so forth. The medical image 12 may be two-dimensional, three-dimensional, or four-dimensional (e.g., a cinematic or CINE sequence tracking uptake and/or washout of a vascular bolus injection).

As used herein, the term "medical subject" encompasses hospital patients, out-patients (e.g., patients not admitted to the hospital but under medical care), clinical study subjects, medical screening subjects, veterinary subjects, and so forth. The medical image 12 is designed to elicit relevant information about a medical condition of the medical subject. In the illustrative case of an oncology medical subject, the medical image 12 is typically designed to elicit structural and/or functional information about a lesion that is suspected or known to be a malignant tumor. In some suitable embodiments the MR modality is used in conjunction with a vascular magnetic contrast agent to obtain functional information about uptake and washout to/from the lesion. Such measurements assess the vascular density and activity of the lesion which is probative of the growth rate of the cancer (since a fast-growing tumor requires an efficient blood supply). The sharpness of the boundary of high vascular activity can also be probative of the presence/absence and extent of metastasis. Additionally or alternatively, the MR imaging may be used to provide anatomical information about the size, shape, and other structural characteristics of the tumor.

For simplicity, reference is made herein to the illustrative medical image 12. However, it is to be understood that typically multiple images may be acquired of the medical subject, using different imaging conditions or sequences (e.g., functional sequences and static anatomical images). Additionally, images may be acquired using two or more modalities. For example, in addition to MR imaging a nuclear imaging technique such as SPECT or PET may be used in conjunction with a tissue-specific radiopharmaceutical tracer in order to assess the presence and distribution of certain type of tissue.

In parallel with the imaging studies, the medical subject also visits a biopsy laboratory 14, where a biopsy procedure is performed in order to extract a tissue sample. The biopsy procedure can be a surgical procedure (incisional biopsy) or can employ a biopsy needle or other interventional instrument. In some embodiments employing an interventional instrument, the biopsy procedure uses a hollow needle that is pushed into the tumor to extract a biopsy "core" whose dimensions correspond to a hollow interior of the biopsy needle. In this approach the structural integrity of the sample is preserved. In other embodiments, the biopsy procedure is a needle aspiration biopsy procedure typically used to extract a fluid or gelatinous tissue sample having limited structural integrity. The resulting extracted tissue is processed to generate one or more biopsy samples for analysis. In the case of a biopsy core or incised tissue sample, this typically entails sectioning the extracted tissue so as to generate a number of biopsy samples for analysis. For example, a biopsy core can be sectioned at multiple placed along the core so as to generate a line of biopsy samples extending along the length of the biopsy core (i.e., along the length of the biopsy needle as placed during tissue extraction). By pressing the needle into the tumor, the resulting line of biopsy samples are acquired at a range of depths into the tumor, which can be useful for assessing any inhomogeneity of the tumor.

The biopsy procedure targets a particular anatomical structure, typically a lesion suspected or known to be malignant in the case of an oncology subject. The lesion may be targeted using various sources of information. If the lesion can be identified externally (e.g., a breast lump suspected of being breast cancer) then targeting the lesion is straightforward. For other lesions, medical images acquired by the medical imaging laboratory 10 may be transferred to the biopsy laboratory 14 and used to target the lesion. However, this approach can be problematic due to difficulty in spatially registering the medical subject with the medical images that may have been acquired days earlier. In some cases, the biopsy laboratory 14 may have an imaging system available to generate current images. In another approach, the biopsy laboratory 14 has an interventional imaging system and the biopsy procedure is an image-guided procedure. In this approach the medical subject is imaged as the interventional instrument is inserted into the patient, and the imaging system enables medical personnel to observe the lesion and the inserted biopsy needle tip simultaneously, enabling precise placement of the needle tip into the lesion.

The biopsy samples generated by the biopsy laboratory 14 are sent to one or more analysis laboratories, such as an illustrative histopathology laboratory 16 and an illustrative molecular testing laboratory 18. These laboratories 16, 18 process the biopsy sample or samples to generate biopsy information, that is, information obtained from the biopsy sample or samples. The histopathology laboratory 16 performs histopathology analyses which typically entail preparing microscope slides containing tissue that is stained by a probative staining agent and visually examining the stained tissue. Based on the staining characteristics, cell morphologies, and other visually perceived information, various forms of histopathology information 20 are generated. For example, by such procedures a skilled histopathologist can readily determine whether the tissue is malignant or benign and, if malignant, may provide information as to the type of cancer, the malignant/benign cellular ratio in the sample, and other cancer characterization useful to the oncologist.

The molecular testing laboratory 18 performs genetic and/or proteomic analyses on the biopsy sample or samples. The analysis may be targeted, e.g. using a microarray or other assay to determine the levels of a specific set of molecular markers followed by computing a result using these levels as inputs. The result may, for example, indicate the type of cancer, activity levels of relevant molecular signaling pathways or networks, or so forth. Additionally or alternatively, a genetic sequencing technique may be applied to measure DNA and/or RNA sequences, optionally up to and including the entire genome of the tissue (i.e., whole genome sequencing or WGS, typically defined as sequencing 95% or more of the entire genome). In some embodiments it is contemplated to sequence DNA or RNA from individual cells, so as (by way of illustrative example) to provide separate genetic profiles for benign and malignant tissues within the tumor. See, e.g. Navin et al., "Tumour evolution inferred by single-cell sequencing", Nature vol. 472 pp. 90-95 (2011). The sequencing dataset generated in WGS or the like is massive, and can be used in conventional molecular tests and/or in "discovery" analysis modalities in which the genetic data is searched in an effort to discover probative genetic features. The output of the molecular testing laboratory 18 is molecular test information 22.

Thus, after completion of the testing the oncologist is provided with medical images 12 and biopsy information such as histopathology information 20 and/or molecular test information 22. In some cases only the histopathology information 20 is generate, whereas in other cases only the molecular test information 22 is generated, whereas in still other cases both histopathology information 20 and molecular test information 22 are generated. It is also to be understood that these various tests may be ongoing for example, the oncology patient may undergo an initial imaging and biopsy sequence in order to assess the initial (i.e., baseline) state of the cancer and to enable the oncologist to design a treatment regimen, possibly including one or more procedures such as chemotherapy, brachytherapy, radiation therapy, or so forth. At intervals during the treatment further imaging and/or biopsy assessments may be performed to assess the effectiveness of the treatment and to enable the treatment to be adjusted. It is still further to be understood that the illustrative laboratory topology of FIG. 1, in which there are separate imaging, biopsy, histopathology, and molecular testing laboratories 10, 14, 16, 18 is merely an illustrative example, and other laboratory topologies can be employed. For example, a single laboratory may perform both histopathology and molecular testing, and in some cases that laboratory may also perform the biopsies. On the other hand, in some embodiments the biopsy laboratory may prepare the histopathology slides, and the histopathology laboratory may include only a few microscopes operated by a skilled histopathologist. As another example, the medical imaging and biopsy laboratories 10, 14 may be combined, as may be useful in order to provide skilled radiologists to operate interventional imaging systems used during image guided biopsy procedures.

Conventionally, the medical images 12 and the biopsy information 20, 22 are processed separately. For example, the radiologist acquires medical images as ordered by the oncologist, and may perform some analysis such as contouring features of interest. The resulting medical images are then passed onto the oncologist for review. Similarly, the histopathologist or other laboratory workers generate the biopsy information 20, 22 in accord with orders from the oncologist, and the biopsy information 20, 22 is also forwarded to the oncologist for review. The oncologist then considers this influx of data in diagnosing the cancer and designing and monitoring a treatment regimen.

With continuing reference to FIG. 1, it is disclosed herein to improve upon this conventional approach by providing an imaging visualization workstation 30 that is configured to perform a method including: spatially registering a biopsy sample extracted from the medical subject with a medical image of the medical subject; combining the medical image with a graphical representation of information generated from the biopsy sample to generate a combined image in which the graphical representation is spatially delineated based on the spatial registration of the biopsy sample; and displaying the combined image on a graphical display device 32 of the imaging visualization workstation. The illustrative workstation 30 is embodied by a computer 34 that includes an electronic data processor (not shown) and suitable user input devices such as an illustrative keyboard 36, a mouse, or so forth. More generally, the imaging visualization workstation 30 may comprise: a notebook computer; a desktop computer; a mobile device such as a smartphone, tablet computer, persona data assistant (PDA), or the like; a network server computer accessible via the Internet and/or a local wired/wireless data network; various combinations thereof; or so forth. While the illustrative display device 32 is a single screen, more generally the display device may comprise two or more screens or display devices, e.g. displaying the same content (mirroring) or displaying different content (e.g., so that a "virtual desktop" extends across the two or more display devices). The display device may also comprise a printer or other electronic marking engine that generates a permanent (monochrome or color) image on paper or another print medium. Further, the electronic data processor of the imaging visualization workstation may be local, e.g. a single-core or multi-core microprocessor and associated electronic components disposed inside the case of a personal computer, desktop computer, tablet computer, or the like, or may be embodied as a distributed electronic data processor, e.g. the workstation may comprise a "dumb terminal" connected via wired and/or wireless link with a network server that performs the electronic data processing.

The disclosed techniques for seamless integration of medical images and biopsy information are also suitably embodied as a non-transitory storage medium storing instructions executable by the illustrative computer 34 or other electronic data processing device to perform the disclosed processing and visualizations. The non-transitory storage medium storing the executable instructions may, for example, include: a hard disk drive or other magnetic storage medium; an optical disk or other optical storage medium; a flash memory, random access memory (RAM), read-only memory (ROM), or other electronic storage medium; or so forth.

With continuing reference to FIG. 1, in order to integrate biopsy information with medical images the imaging visualization workstation 30 implements a biopsy sample registration module 40 that spatially registers each biopsy sample extracted from the medical subject with the medical image of the medical subject. The spatial registration utilizes locational information for biopsy samples 42 provided by the biopsy laboratory 14. This information can be varied, and thus provides varying levels of spatial registration (i.e., varying levels of spatial localization of the biopsy sample respective to the imaged area). In some embodiments, the localization information 42 merely identifies from which lesion the biopsy sample was extracted. In this case the biopsy sample registration module 40 spatially registers the biopsy sample by associating it with the lesion from which it was extracted. In other embodiments the localization information 42 is more detailed, for example optionally including an interventional image that was acquired of the interventional instrument positioned to obtain the biopsy sample. In such cases, the spatial registration of the biopsy sample can be more precise. After spatial registration, a medical image/biopsy information integration module 44 implemented by the workstation 30 combines the medical image 12 with a graphical representation of information 20, 22 generated from the biopsy sample to generate a combined image in which the graphical representation is spatially delineated based on the spatial registration of the biopsy sample. An image display module 46 implemented by the workstation 30 displays the combined image on the display device 32.

This approach provides an integrated display that enables the oncologist to consider the imaging and biopsy information concurrently, as an integrated unit. Moreover, as disclosed in illustrative examples herein, this combination can synergistically enhance the information above and beyond that provided by either imaging alone or biopsy alone. For example, the more detailed spatial information provided by the imaging can be leveraged to extend the spatial content of the biopsy information. Conversely, the biopsy information can be used to resolve an apparently homogeneous lesion into heterogeneous components.

Figure 2:
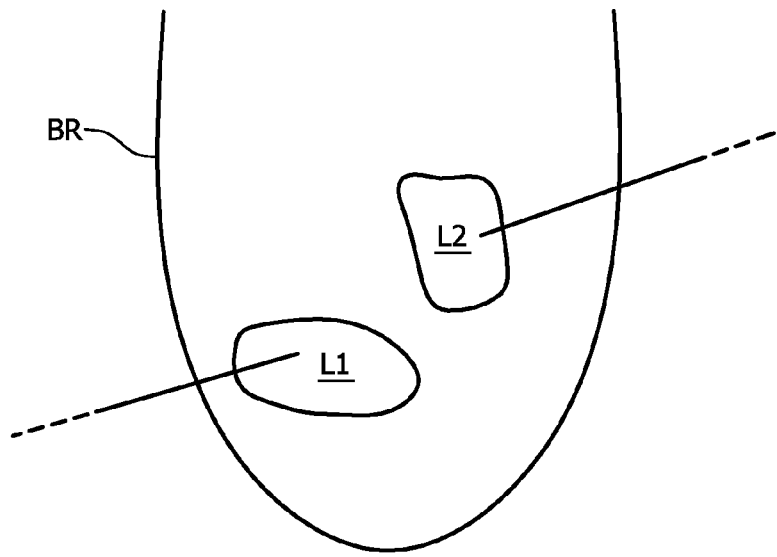
Figure 3:
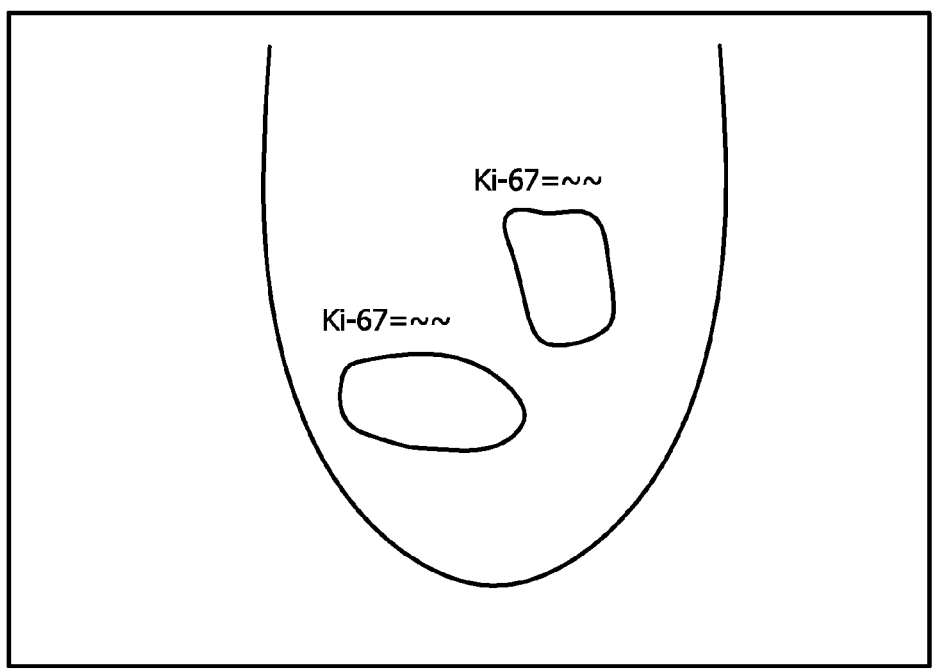
Figure 4:
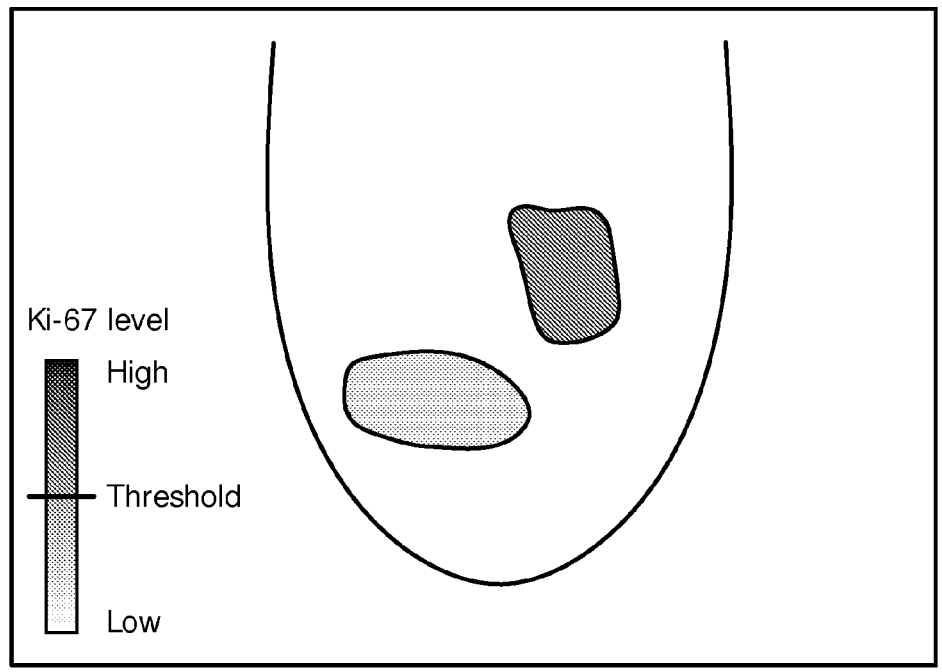
Figure 5:
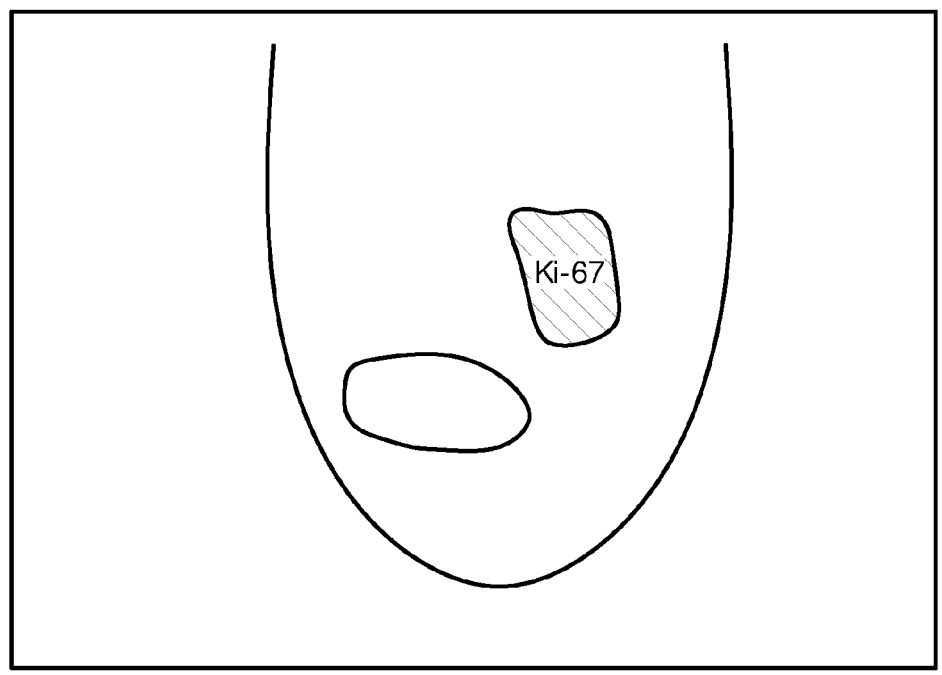

With continuing reference to FIG. 1 and with further reference to FIGS. 2-5, some illustrative examples are set forth in which the locational information 42 is limited to identifying the lesion from which the biopsy sample is extracted. In this case, the spatial registration module 40 associates the biopsy sample with a depiction of the lesion in the medical image 12. This is straightforward since the radiologist typically contours or otherwise segments the lesion or lesions of interest, and the locational information 42 provided by the biopsy laboratory includes identification of the lesion from which the biopsy sample was extracted. For example, FIG. 2 shows a breast BR with two lesions L1, L2. A biopsy procedure collecting biopsy samples from both lesions is diagrammatically indicated by interventional instrument tips shown sampling each lesion indicated (diagrammatically by a line representing a biopsy needle). In the illustrative example, molecular testing and/or histopathology is applied to the biopsy sample of each lesion L1, L2 to determine the expression level of the antigen Ki-67 in the respective lesions. Ki-67 is a cell proliferation marker that is associated with cancer proliferation. The Ki-67 level can therefore be expected to be indicative of the aggressiveness of the cancer, that is, whether and how fast it spreads or metastasizes. FIG. 3 shows an example of a medical image showing the lesions L1, L2 (which are not labeled in FIG. 3 for clarity, but compare with FIG. 2) and showing the measured Ki-67 expression level as a graphical representation in which each lesion is annotated numerically at a position proximate to the lesion (specifically, above the lesion in the example of FIG. 3 using the textual annotation "Ki-67=~~~~" where "~~~~" generically denotes the quantitative Ki-67 expression level. FIG. 4 shows another graphical representation in which the Ki-67 level for each lesion determined by biopsy is indicated by false coloring or highlighting. In false coloring, a color scale is used to indicate the Ki-67 level (for example, red may indicate the highest Ki-67 level on the scale and blue may indicate the lowest Ki-67 level on the scale). In highlighting, the intensity or texture of the lesion is set to indicate the Ki-67 level. Highlighting is useful if the graphical display device 32 is a monochrome display device. The color or highlight is determined by the information generated from the biopsy sample (namely the Ki-67 expression level in this example). The image of FIG. 4 also includes a scale legend in the lower left-hand corner that indicates the correspondence between the false color or highlight and the Ki-67 expression level. The scale legend also shows a threshold indicating a Ki-67 expression level above which the lesion is deemed to be suspected cancer or cancer type. As seen in FIG. 4, lesion L2 (again, as labeled in FIG. 2) has a substantially higher Ki-67 expression level than lesion L1. FIG. 5 shows yet another graphical representation in which false coloring or highlighting is applied in a binary manner, that is, any lesion that has a Ki-67 expression level above the threshold for concern as indicated by biopsy information (namely lesion L2 in this example) is false colored or highlighted while any lesion that is does not have a Ki-67 expression level above the threshold is not false-colored or highlighted. This graphical representation provides less information compared with the approaches of FIGS. 3 and 4, but is more likely to attract the oncologist's attention to the high Ki-67 expression level in the lesion L2.

A more general example of operation of a system in which the biopsy sample is spatially registered to (i.e. associated with) a lesion is as follows. The oncologist loads the medical image. In the imaging data, a lesion L is characterized by an image features vector $P_I(L)=[I_1, I_2, \ldots, I_f]^T$ (where there are f imaging features $I_1, \ldots, I_f$ in the vector, and the superscript "T" denotes transpose). The image is suitably downloaded from a Picture Archiving and Communication System (PACS). For the same patient and the same lesion, the oncologist loads molecular test results $P_M(L)=[M_1, M_2, \ldots, M_g]^T$ (where there are g molecular test results $M_1, \ldots, M_g$ in the vector, and the superscript "T" again denotes transpose). It should be noted that the molecular test results vector $P_M(L)$ may be a subset of the total set of molecular tests performed on the biopsy sample or samples extracted from lesion L. The correlation of the two features vectors $P_I(L)$ and $P_M(L)$ is provided by the spatial registration module 40. In some embodiments, when the medical image is displayed and the oncologist selects a particular lesion L (for example, by clicking on the lesion L using a mouse), the contents of the feature vectors $P_I(L)$ and $P_M(L)$ are queried and presented as a pop-up table or other suitable representation.

Another, more specific, example of operation of a system in which the biopsy sample is spatially registered to (i.e. associated with) a lesion is as follows. This example integrates an imaging feature, namely the blooming index (BI) measured by MRI using a vascular bolus injection, with a molecular test result, namely the vascular endothelial growth factor (VEGF) level information. Blooming is a characterization of the margin of a mass over time. Blooming describes a fast-enhancing mass with initially sharply delineated borders that become un-sharp several minutes after the bolus injection of a contrast agent. The degree to which the margin blurs into the background indicates the amount of blooming present. The degree of blooming is expected to positively correlate with angiogenesis. Early signs of blooming can be evaluated by detecting low-level peripheral enhancement on the subtraction image derived from a post-contrast image and the pre-contrast image. Using a single, pre-configured post-contrast image that occurs at (or near) peak enhancement reduces adverse effects of motion and other time-varying image artifacts. A blooming index (BI) is computed as integral values in the range of [0, 25]. See Penn et al., "Morphologic Blooming in Breast MRI as a Characterization of Margin for Discriminating Benign from Malignant Lesions," Acad Radiol 2006; 13:1344-1354; Fisher et al., "Is the 'blooming sign' a promising additional tool to determine malignancy in MR mammography?" Eur Radiol (2004) 14:394-401). A higher BI value indicates a greater amount or degree of bloom. Under this imaging test, a lesion is considered suspicious if BI•7. The blooming index is evaluated on a slice-by-slice basis in the primary plane of acquisition on all possible lesions larger than a threshold size (e.g., larger than 8 mm). When suspicious possible lesions overlap on adjacent slices, they are merged into three-dimensional clusters.

Vascular endothelial growth factor (VEGF) is a signal protein produced by cells that stimulates vasculogenesis and angiogenesis. It is part of the system that restores the oxygen supply to tissues when blood circulation is inadequate. The normal function of VEGF is to create new blood vessels during embryonic development, new blood vessels after injury, muscle following exercise, and new vessels (collateral circulation) to bypass blocked vessels. However, when VEGF is overexpressed, it can contribute to disease. Solid cancers cannot grow beyond a limited size without an adequate blood supply; cancers that can express VEGF are able to grow and metastasize. Overexpression of VEGF can cause vascular disease in the retina of the eye and other parts of the body. Drugs such as bevacizumab can inhibit VEGF and control or slow those diseases.

Since both high blooming factor (BI) and VEGF overexpression are linked to high angiogenesis rate associated with some cancers, it is reasonable to expect the BI and VEGF level to have some correlation. By employing a combined image display such as those shown in FIGS. 3-5 (but with the annotated value, false coloration, or highlighting being associated with VEGF and blooming index, e.g. using numeric values for VEGF and false coloration for BI or vice versa) the oncologist can readily assess both metrics to provide confirmation of a high angiogenesis rate suggestive of high cancer growth. The VEGF expression level can be assessed based on the biopsy using various techniques. In a histopathology approach, a biopsy sample is stained and examined under a microscope by a trained pathologist to assess the VEGF quantitatively. Alternatively, substantially equivalent information can be obtained from genetic sequencing data. In one approach, a readout of all the genes in the VEGF pathway is obtained from sequencing data generated from a biopsy sample, and a correlation is performed between a vector of genomic (transcriptomic or methylation) features against a vector of imaging features (e.g. the blooming index as described above, and optionally other pertinent features such as tumor volume and/or shape). A correlation vector is generated instead of correlation value for each patient.

As another example, the imaging can correlate image texturing associated with cell adhesion with molecular markers associated with cell adhesion. One cell function is the binding of a cell to a surface, extracellular matrix or another cell using cell adhesion molecules. There are multiple genes (or, when expressed, proteins) involved such as selectins, integrins, and cadherins. Proper adhesion maintains multicellular structure, and disregulation of this function is expected to be linked to tumorigenesis. These molecules are also involved in signal transduction. On the biopsy side, genomic features can be assessed based on their role in adhesion. For example, a genomic vector can include the levels of all adhesion molecules. On the imaging side, different types of texture features are suitably assessed to identify correlations between certain sets of adhesion molecules and a resulting irregular texture in the imaged tumor. Conversely, if a clinician notices certain imaging features such as a particular texture type, this can be further investigated based on sequencing of tumor biopsy samples to generate molecular features associated with adhesion (e.g., expressed as a genomic vector as just described). In this example, the information generated from the biopsy sample (namely the genomic vector of adhesion-related genes or a result derived from that information, such as an activity level for an adhesion-related pathway or network) is suitably displayed numerically as per the example of FIG. 3, and image enhancement such as false coloring or highlighting is suitably used to indicate areas of the image that exhibit the particular texture type under investigation. In this way, the clinician can readily assess whether there is a positive correlation between disregulation of the adhesion function as indicated by the textually represented biopsy information and image texturing indicated by highlighting or false coloration.

In the foregoing examples, the biopsy sample is spatially registered to (i.e. associated with) a lesion. However, if the available locational information 42 is sufficient, the spatial registration of the biopsy sample can be more finely grained, e.g. a biopsy sample can be associated with a particular portion of a lesion. Some examples of ways this can be done follow.

Figure 8:
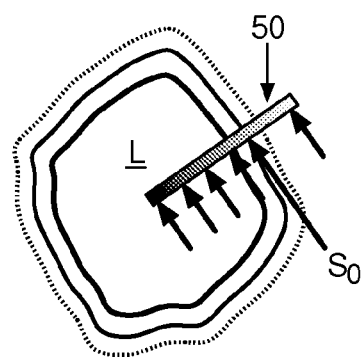

With reference to FIGS. 6-8, a biopsy core 50 obtained using a hollow biopsy needle is shown. The biopsy core 50 has length $L_{core}$, and six biopsy samples $S_0$, $S_1$, $S_2$, $S_3$, $S_4$, and $S_R$ are generated by sectioning the biopsy core 50 as indicated in FIG. 6. As shown in FIG. 7, the biopsy core 50 is obtained by pressing the hollow biopsy needle into the lesion L along a trajectory 52. The lesion L has a boundary that is not abrupt but rather has a finite transition of width $W_b$. (In some other examples, the lesion boundary may be abrupt). In performing the sectioning, the skilled technician examples the biopsy core 50 under a microscope and can thereby identify the transition of width $W_b$. Based on this observation, the technician performs sectioning to obtain a biopsy sample $S_0$ at the center of the boundary width $W_b$ and obtains biopsy samples $S_1$, $S_2$, $S_3$, and $S_4$ at progressively larger depths into the lesion L. Additionally, as tissue from outside the lesion L is available, the technician obtains a reference biopsy sample $S_R$. The biopsy samples $S_R$, $S_0$, $S_1$, $S_2$, $S_3$, and $S_4$ thus form a line of biopsy samples. In this case, the locational information 42 of FIG. 1 includes the information that sample $S_0$ is located at the boundary of the lesion L (thus providing a reference feature for the spatial registration), the known biopsy needle trajectory 52, and the known length $L_{core}$ of the biopsy core 50, as well as the known locations of the biopsy samples $S_R$, $S_0$, $S_1$, $S_2$, $S_3$, and $S_4$ along that length. As shown in FIG. 8, this information is sufficient to spatially register the biopsy core 50 and the biopsy samples $S_R$, $S_0$, $S_1$, $S_2$, $S_3$, and $S_4$ respective to a depiction of the lesion L in the medical image 12.

Figure 9:
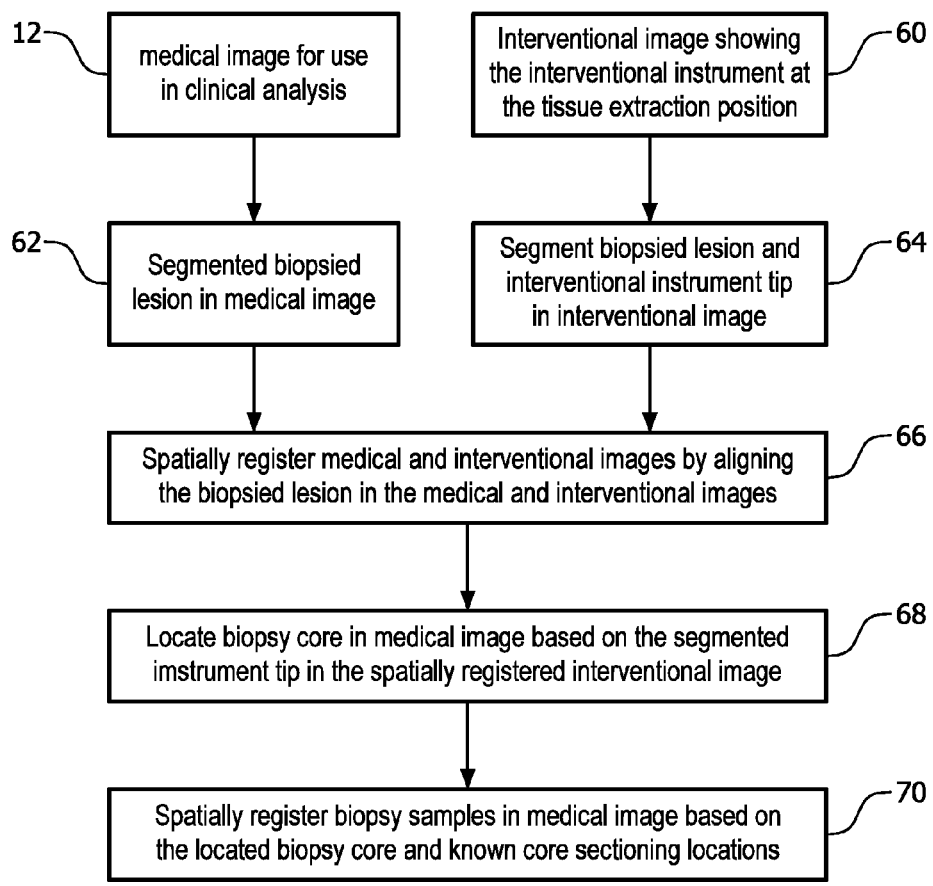
FIG. 9 shows a flow chart of another approach for spatial registering a biopsy sample with a medical image, which makes use of an interventional image showing the interventional instrument at the tissue extraction position.

With reference to FIG. 9, another approach for spatially registering a biopsy sample is described, which utilizes an interventional image. As already discussed, the medical image 12 is designed for use in clinical analysis, and as such is typically of high spatial resolution and/or employs a contrast mechanism (such as vascular contrast agent bolus injection) that yields probative information. In this example the biopsy sample is acquired by an image-guided biopsy procedure. The interventional imaging system employed in the image guidance is typically of relatively low resolution it is sufficient to resolve the tip of the biopsy needle and the lesion with sufficient resolution to accurately position the needle tip in the lesion. Moreover, the interventional imaging typically does not employ special contrast mechanisms (although the use of a tracking micro-coil or other active or passive marker disposed on or in the tip of the interventional instrument is contemplated). Thus, the interventional images obtained during the image-guided biopsy procedure are usually of little or no clinical value, and are not normally utilized except for the image guidance. In the spatial registration approach of FIG. 9, however, an interventional image 60 showing the interventional instrument at the tissue extraction position is supplied to the spatial registration module 40 as (at least part of) the locational information 42 (see FIG. 1). In an operation 62 the depiction of the biopsied lesion in the medical image 12 is segmented, either manually (e.g., by manual contouring of the lesion) or automatically, or by a semi-automatic approach. In an operation 64 the interventional image 60 is similarly segmented to delineate the biopsied lesion and the interventional instrument tip. In an operation 66, the medical image 12 and the interventional image 60 are spatially registered by aligning the segmented biopsied lesion in the two images. In an operation 68, the biopsy core extracted by the hollow biopsy needle (e.g., the biopsy core 50 of FIG. 6) is located in the medical image based on the segmented instrument tip in the spatially registered interventional image. (This is based on the recognition that the biopsy core 50 is disposed inside the hollow biopsy needle tip at the extraction position). In an operation 70, the individual biopsy samples sectioned from the biopsy core 50 are spatially registered with the medical image 12 based on the located biopsy core and the known sampling locations (e.g., sampling locations $S_R$, $S_0$, $S_1$, $S_2$, $S_3$, $S_4$) along the line of the biopsy core.

Figure 10:
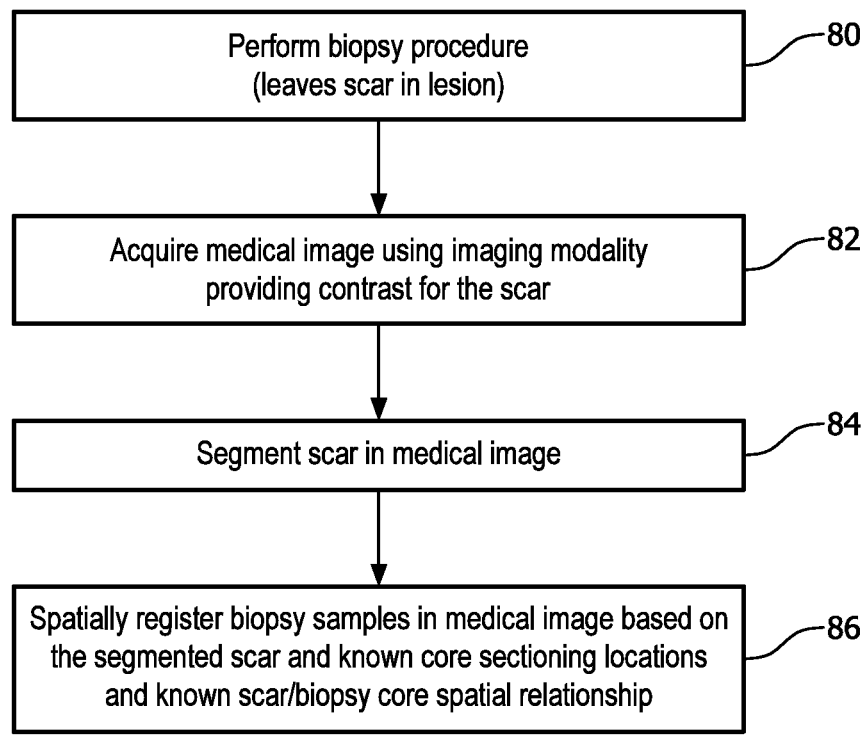
FIG. 10 shows a flow chart of another approach for spatial registering a biopsy sample with a medical image, which makes use of biopsy scar that is visible in the medical image.

With reference to FIG. 10, yet another approach for spatially registering a biopsy sample is described. This approach is appropriate if the biopsy is performed before the medical image 12 is acquired, and if the biopsy procedure leaves a biopsy scar in the lesion that is visible in the medical image 12. In this case, the approach of FIG. 10 is as follows. The biopsy procedure is performed first in an operation 80. This biopsy procedure 80 leaves a biopsy scar in the lesion. In an operation 82 the medical image 12 is acquired, using an imaging modality for which the biopsy scar is visible. In an operation 84 the biopsy scar is segmented (again, using manual, automatic, or semi-automatic segmentation). In an operation 86, the biopsy samples are spatially registered with the medical image 12 based on the segmented biopsy scar and known biopsy core section locations along the core (e.g., sampling locations $S_R$, $S_0$, $S_1$, $S_2$, $S_3$, $S_4$ of FIG. 6) and a known spatial relationship between the biopsy scar and the biopsy core. This known relationship may be precisely one-to-one, i.e. the core precisely matching the imaged biopsy scar; however, it is alternatively contemplated to employ a spatial transform to accommodate shrinkage or other known scar distortion mechanisms.

The spatial registration approaches described with reference to FIGS. 6-10 provide finer-grained spatial localization of a biopsy sample to a region smaller than the lesion as a whole. However, the biopsy sample (e.g., biopsy samples $S_1$, $S_2$, $S_3$, $S_4$ of FIGS. 6-8) are only along a line and do not map out the volume of the lesion. However, in embodiments described herein the spatial imaging data provided by the medical image 12 is leveraged to enable the biopsy samples to provide characterization of volumetric regions of the lesion.

With reference to FIG. 11, in one approach the lesion is assumed to have approximately spherical symmetry. Thus, the biopsy sample $S_1$ is assumed to be representative of an isocontour shell 90 corresponding to the depth of the biopsy sample $S_1$ in the lesion L. In the same way, the biopsy sample $S_2$ is assumed to be representative of an isocontour shell 92 inside the isocontour shell 90 and corresponding to the depth of the biopsy sample $S_2$ in the lesion L. The biopsy sample $S_3$ is assumed to be representative of an isocontour shell 94 inside the isocontour shell 92 and corresponding to the depth of the biopsy sample $S_3$ in the lesion L. Finally, the deepest biopsy sample $S_4$ is assumed to be representative of a central roughly spherical core 96 inside the isocontour shell 94. The four regions 90, 92, 94, 96 defined in the lesion L are suitably false colored, highlighted, or labeled based on biopsy information obtained from the corresponding four biopsy samples $S_1$, $S_2$, $S_3$, $S_4$ sectioned from the biopsy core 50. More generally, the image location containing the biopsy sample is extended to a contiguous (i.e. connected) region containing the biopsy sample based on suitable assumptions or spatial modeling of the lesion (in the case of FIG. 11, the assumption is that the lesion L has approximately spherical symmetry where the deviation from perfect spherical symmetry follows the deviation of the boundary of the lesion L from perfect spherical symmetry). FIG. 11 shows a legend at the top of the display identifying the meaning of the various false colors or highlights. FIG. 11 also shows the biopsy core 50 and labels the four biopsy samples $S_1$, $S_2$, $S_3$, $S_4$—however, these items would typically not be displayed to the oncologist.

With reference to FIGS. 12 and 13, in another approach for extending the discrete biopsy samples across the lesion operates by (1) identifying an image characteristic at the location of the medical image spatially registered with the biopsy sample and (2) defining a region of the medical image associated with the biopsy sample as one or more portions of the medical image having the identified image characteristic. FIG. 12 illustrates an example using the biopsy sample $S_2$ obtained from the biopsy core 50 of FIG. 6. The image characteristic at the location of the medical image in this example is diagrammatically indicated by a darker contrast as compared with other areas of the lesion L. More generally, the image characteristic can be any image feature of interest that is present at the location of the biopsy sample $S_2$, such as a characteristic intensity level, a characteristic texturing or other micromorphology, a particular value for bolus intake measured in an image sequence, or so forth. To extend the range of the region associated with and containing the biopsy sample $S_2$, the integration module 44 searches the medical image 12 to identify other portions of the image that also exhibit this image characteristic (within a suitable tolerance). In the example of FIG. 12, it is seen that there are four distinct portions or sub-regions 100 having the image characteristic of the location of the biopsy sample $S_2$. FIG. 13 illustrates a modified version of the medical image 12 that includes the biopsy information from biopsy sample $S_2$ as a false coloration or highlighting (diagrammatically indicated by crosshatching in FIG. 13) of the identified regions 100 associated with the biopsy sample $S_2$. The modified image of FIG. 13 also includes a legend in the upper right corner identifying the significance of the false coloration or highlighting.

With reference to FIGS. 14 and 15, the information generated from the biopsy sample may comprise information generated from the biopsy sample and also from content of the medical image. Said another way, the information generated from the biopsy sample and displayed on the modified or combined image may constitute information generated by a mathematical or other combination of biopsy and imaging data. In the example of FIG. 14, processing of biopsy samples is used to generate biopsy information that includes microvasculature information for lesion tissue. As already noted, the vascular endothelial growth factor (VEGF) signal protein is a molecular marker that is indicative of angiogenesis rate, i.e. higher VEGF expression typically correlates with a higher angiogenesis rate. Regions of higher angiogenesis rate may be expected to have higher microvasculature density. If the biopsy sample is large enough, a more direct approach for estimating the microvasculature information is to measure the microvasculature density for biopsy samples $S_1$, $S_2$, $S_3$, $S_4$ at different depths into the lesion L (again using the illustrative biopsy core of FIG. 6 as an example). Assuming the generally spherical model of FIG. 11, this enables estimation of the microvasculature density as a function of depth inside the lesion L. With this detailed microvasculature density information and the known structure of the lesion L as provided by the medical image 12, a spatial map of chemotherapy accessibility to the lesion L can be estimated. Since it is assumed that the chemotherapy drug is delivered via the microvasculature, the map of chemotherapy accessibility can also be thought of (with suitable magnitude scaling) as a blood perfusion map for the lesion. FIG. 14 diagrammatically illustrates a combined image comprising the estimated spatial map of chemotherapy accessibility to the lesion L superimposed onto the medical image 12. In this example, it is seen that chemotherapy access is high for the outer portion of the lesion L and decreases deeper inside the lesion such that the innermost portion of the lesion L has the lowest chemotherapy access. Such a map could result from low microvascular density deep inside the lesion (where the tissue may be stagnant or even partially necrotic) and higher microvascular density near the boundary of the lesion L where the cancer is proliferating. FIG. 14 also includes a scale legend in the upper right corner.

Another example, also depicted in FIG. 14, applies to planning brachytherapy rather than chemotherapy. Brachytherapy entails implantation of radioactive seeds in or proximate to the tumor with the expectation that radiation released from the seeds over time will suppress the malignancy. In this case, relevant information obtained from the biopsy sample may include a radiation absorption characteristic of lesion tissue for radiation emitted by a brachytherapy radiation seed. For example, the radiation absorption characteristic may be quantified as a radiation absorption coefficient, an extinction coefficient for the radiation, a transmissivity coefficient for the radiation, or so forth. These values may be measured on the biopsy sample directly using suitable equipment, or alternatively may be determined from the tissue type and/or tissue density using a lookup table or the like. FIG. 14 diagrammatically shows a combined image in which an optimal placement of brachytherapy radiation seeds respective to the lesion is shown superimposed on the medical image. The optimal placement is determined based on the depiction of the lesion in the medical image and the radiation absorption characteristic of lesion tissue. The optimal placement is chosen to provide a desired radiation exposure through the volume of the lesion, with the exposure at any particular location in the lesion being computed based on the proximity of the radiation seed(s) and the computed absorption (e.g., computed as an integral of the absorption characteristic over the space separating the radiation seed from the location where exposure is being computed). In FIG. 14, the optimal placement of brachytherapy seeds is indicated by superimposing icons (namely filled circle icons) representing the radiation seeds.

For conciseness, FIG. 14 depicts both the chemotherapy access map and the optimal placement of brachytherapy seeds. Of course, if only chemotherapy is contemplated then the brachytherapy seed placement overlay is suitably not computed or displayed, and likewise of only brachytherapy is contemplated then the chemotherapy access map is suitably not computed or displayed. In some embodiments both chemotherapy and brachytherapy may be planned, in which case the display shown in FIG. 14 is suitable. If only brachytherapy is planned, then the chemotherapy access map may be replaced by a map of estimated radiation dosage density computed for the optimal placement of brachytherapy seeds and the radiation absorption characteristic determined from the biopsy sample. While two specific mapping examples have been mentioned (the chemotherapy access map shown in FIG. 14, and a radiation dosage map suitably computed for the optimal radiation seed placement), the skilled artisan will readily recognize that these examples can be generalized to a procedure comprising: computing a map of a derived characteristic for the lesion wherein the derived characteristic depends upon the biopsy information and spatial location within the lesion; and displaying the map of the derived characteristic superimposed on the medical image.

FIG. 15 illustrates another example, in which future lesion growth is projected based on a combination of lesion tissue growth rate estimated from biopsy samples and the present size and shape of the lesion as shown by the medical image 12. VEGF expression level determined from the biopsy sample can again be used as a growth rate estimate. Other molecular markers indicative of cellular proliferation rate can additionally or alternatively be measured. Alternatively, histopathology comparison of biopsy sample $S_0$ (taken from the boundary of the lesion L, see FIG. 6) and biopsy samples $S_1$, $S_2$, $S_3$, and/or $S_4$ (taken from inside the lesion L) can be used to more directly assess the rate of cellular proliferation at the lesion boundary. From the cellular proliferation rate obtained from the biopsy sample(s) and the current lesion boundary shown in the medical image 12, one or more future lesion boundaries can be projected for various times in the future. FIG. 15 shows a combined image showing the current lesion with its boundary (solid line, the current boundary being taken as the middle of the transition region of width $W_b$, see FIGS. 6 and 7) and projected future lesion boundaries for one month in the future (dashed line) and three months in the future (dotted line) superimposed onto the medical image 12. In illustrative FIG. 15, the medical image 12 is shown at reduced intensity, i.e. "grayed out" in FIG. 15, so as to emphasize the projected lesion growth. A legend in the lower left corner identifies the line types.

It should be noted that the future growth estimates are for the cell proliferation rate estimated from the biopsy samples—this rate would not take into account any oncological therapy that is applied subsequent to the biopsy procedure. Thus, for example, if the biopsy procedure was performed before the therapy regimen was initiated then the projected lesion growth shown in FIG. 15 represents the expected growth without therapy. A useful workflow would then be to initiate the therapy regimen and to acquire an image of the actual tumor at one month and three months in the future. Comparison of those images with the projected tumor sizes at one- and three-months shown in FIG. 15 then would provide an effective graphical indication of the effectiveness of the therapy, e.g. if the lesion has grown but at a rate less than that projected in FIG. 15, this may indicate the therapy has some effectiveness even though it is not actually causing shrinkage of the tumor (i.e., the therapy is causing the tumor to grow less rapidly).

The examples set forth herein are provided for illustrative purposes. The skilled artisan, upon reading and understanding the disclosure herein including the illustrative examples, can readily employ the disclosed imaging visualization workstation and/or the disclosed techniques for seamlessly integrating imaging and biopsy data to provide other synergistic configurations that are probative for various types of oncology applications as well as various other clinical and/or veterinary applications. For example, the disclosed techniques can readily be applied to cardiology so as to seamlessly integrate cardiac images (optionally employing a vascular contrast agent bolus to dynamically image blood flow through the heart and major vasculature) with information related to cardiac function obtained by processing biopsy samples, such as monitoring of natriuretic peptide levels (e.g., BNP, ANP, or so forth), in order to provide reinforcement or extension of the information obtained by either imaging or biopsy alone.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:
1. An apparatus comprising:
an imaging visualization workstation including a graphical display device and an electronic data processor, the imaging visualization workstation being configured to perform a method including:
spatially registering a biopsy sample extracted from a lesion of a medical subject with a medical image of the medical subject by identifying a region of the medical image of the medical subject that depicts a location of the medical subject from which the biopsy sample was extracted, by the electronic data processor,
combining the medical image with a graphical representation of information generated from the biopsy sample to generate a combined image in which the graphical representation is spatially delineated based on the spatial registration of the biopsy sample by the electronic data processor, wherein the information generated from the biopsy sample includes microvasculature information for lesion tissue, and wherein the combining includes:
estimating a spatial map of chemotherapy accessibility to the lesion based on the depiction of the lesion in the medical image and the microvasculature information for lesion tissue, and generating the combined image comprising the estimated spatial map of chemotherapy accessibility to the lesion superimposed onto the medical image; and displaying the combined image on the graphical display device of the imaging visualization workstation.

2. The apparatus of claim 1 wherein:

the spatially registering associates the biopsy sample with a depiction of the lesion in the medical image; and the combined image associates the graphical representation of information generated from the biopsy sample with the depiction of the lesion in the medical image.

3. The apparatus of claim 2 wherein the combining comprises at least one of: labeling the depiction of the lesion in the medical image with the information generated from the biopsy sample extracted from the lesion, and false coloring or highlighting the depiction of the lesion in the medical image with a color or highlight determined by the information generated from the biopsy sample.

4. The apparatus of claim 1 wherein the biopsy sample comprises a section of extracted tissue, and the spatial registering comprises:

identifying a reference feature in the medical image; and locating the extracted tissue in the medical image based on the reference feature.

5. The apparatus of claim 4 wherein the reference feature comprises a lesion boundary.

6. The apparatus of claim 4 wherein the reference feature comprises a biopsy scar.

7. The apparatus of claim 1 wherein the biopsy sample is obtained using an interventional instrument and an interventional image is acquired of the interventional instrument positioned to obtain the biopsy sample, and the spatial registering comprises:

spatially registering the medical image and the interventional image; and locating the biopsy sample in the medical image based on the spatially registered interventional image.

8. The apparatus of claim 1 wherein the combining further comprises:

defining a region of the medical image depicting a portion of the medical subject from which the biopsy sample was extracted according to the spatial registering; and modifying the region of the medical image to delineate the region and to indicate the information generated from the biopsy sample.

9. The apparatus of claim 8 wherein the biopsy sample comprise a line of biopsy samples extracted from different depths in a lesion and the defining comprises:

for each biopsy sample, defining the region based on a size and a shape of the lesion wherein the defined region is a contiguous region.

10. The apparatus of claim 8 wherein the defining comprises:

identifying an image characteristic at the location of the medical image spatially registered with the biopsy sample; and defining the region of the medical image as one or more portions of the medical image having the identified image characteristic.

11. The apparatus of claim 1 wherein the information generated from the biopsy sample further includes lesion tissue growth rate, and the combining comprises:

projecting one or more future lesion boundaries based on the depiction of the lesion in the medical image and the lesion tissue growth rate; and generating the combined image comprising the projected one or more future lesion boundaries superimposed onto the medical image.

12. The apparatus of claim 1 wherein the information generated from the biopsy sample further includes radiation absorption characteristic of lesion tissue for radiation emitted by a brachytherapy radiation seed, and the combining further comprises:

computing an optimal placement of brachytherapy radiation seeds respective to the lesion based on the depiction of the lesion in the medical image and the radiation absorption characteristic of lesion tissue; and generating the combined image comprising the optimal placement of brachytherapy radiation seeds superimposed onto the medical image.

13. A method comprising:

spatially registering a biopsy sample extracted from a lesion of a medical subject with a medical image of the medical subject by identifying a region of the medical image of the medical subject that depicts a location of the medical subject from which the biopsy sample was extracted;

combining the medical image with a graphical representation of information generated from the biopsy sample to generate a combined image in which the graphical representation is spatially delineated based on the spatial registration of the biopsy sample wherein the information generated from the biopsy sample includes microvasculature information for lesion tissue, and wherein the combining includes:

estimating a spatial map of chemotherapy accessibility to the lesion based on the depiction of the lesion in the medical image and the microvasculature information for lesion tissue, and generating the combined image comprising the estimated spatial map of chemotherapy accessibility to the lesion superimposed onto the medical image; and displaying the combined image on a graphical display device.

14. A non-transitory storage medium storing instructions executable by an electronic data processing device to perform operations including spatially registering a biopsy sample extracted from a medical subject with a medical image of the medical subject by identifying a region of the medical image of the medical subject that depicts a location of the medical subject from which the biopsy sample was extracted; and combining the medical image with a graphical representation of information generated from the biopsy sample to generate a combined image in which the graphical representation is spatially delineated based on the spatial registration of the biopsy sample, wherein the information generated from the biopsy sample includes radiation absorption characteristic of lesion tissue for radiation emitted by a brachytherapy radiation seed, and wherein the combining includes:

computing an optimal placement of brachytherapy radiation seeds respective to the lesion based on the depiction of the lesion in the medical image and the radiation absorption characteristic of lesion tissue, and generating the combined image comprising the optimal placement of brachytherapy radiation seeds superimposed onto the medical image; and displaying the combined medical image on a graphical display device.

15. At least one non-transitory computer-readable medium comprising instructions that, in response to execution of the instructions by one or more processors, cause the one or more processors to perform the following operations:

spatially registering a biopsy sample extracted from a medical subject with a medical image of the medical subject by identifying a region of the medical image of the medical subject that depicts a location of the medical subject from which the biopsy sample was extracted;

combining the medical image with a graphical representation of information generated from the biopsy sample to generate a combined image in which the graphical representation is spatially delineated based on the spatial registration of the biopsy sample, wherein the information generated from the biopsy sample includes microvasculature information for lesion tissue, and wherein the combining includes:

estimating a spatial map of chemotherapy accessibility to the lesion based on the depiction of the lesion in the medical image and the microvasculature information for lesion tissue; and generating the combined image comprising the estimated spatial map of chemotherapy accessibility to the lesion superimposed onto the medical image; and displaying the combined medical image on a graphical display device.

16. The at least one non-transitory computer-readable medium of claim 15, wherein:

the spatially registering associates the biopsy sample with a depiction of the lesion in the medical image; and the combined image associates the graphical representation of information generated from the biopsy sample with the depiction of the lesion in the medical image.

17. The at least one non-transitory computer-readable medium of claim 15, wherein the combining comprises at least one of: labeling the depiction of the lesion in the medical image with the information generated from the biopsy sample extracted from the lesion, or false coloring or highlighting the depiction of the lesion in the medical image with a color or highlight determined by the information generated from the biopsy sample.

18. A method comprising:

spatially registering a biopsy sample extracted from a medical subject with a medical image of the medical subject by identifying a region of the medical image of the medical subject that depicts a location of the medical subject from which the biopsy sample was extracted; and combining the medical image with a graphical representation of information generated from the biopsy sample to generate a combined image in which the graphical representation is spatially delineated based on the spatial registration of the biopsy sample, wherein the information generated from the biopsy sample includes radiation absorption characteristic of lesion tissue for radiation emitted by a brachytherapy radiation seed, and wherein the combining includes:

computing an optimal placement of brachytherapy radiation seeds respective to the lesion based on the depiction of the lesion in the medical image and the radiation absorption characteristic of lesion tissue, and generating the combined image comprising the optimal placement of brachytherapy radiation seeds superimposed onto the medical image; and displaying the combined medical image on a graphical display device.

* * * * *